United States Patent [19]
Grundler et al.

[11] Patent Number: 6,096,758
[45] Date of Patent: Aug. 1, 2000

[54] 3-METHYLIMIDAZOPYRIDINES

[75] Inventors: Gerhard Grundler; Jörg Senn-Bilfinger, both of Constance, Germany

[73] Assignee: Byk Gulden Lomberg Chemische Fabrik GmbH, Constance, Germany

[21] Appl. No.: 09/117,139

[22] PCT Filed: Jan. 24, 1997

[86] PCT No.: PCT/EP97/00333

§ 371 Date: Jul. 24, 1998

§ 102(e) Date: Jul. 24, 1998

[87] PCT Pub. No.: WO97/27192

PCT Pub. Date: Jul. 31, 1997

[30] Foreign Application Priority Data

Jan. 26, 1996 [DE] Germany ............... 196 02 855
Feb. 7, 1996 [EP] European Pat. Off. ............... 96101728

[51] Int. Cl.$^7$ ....................... A61K 31/435; C07D 471/04
[52] U.S. Cl. ............................................. 514/300; 546/121
[58] Field of Search .............................. 546/121; 514/300

[56] References Cited

FOREIGN PATENT DOCUMENTS

WO 95/10518   4/1995   WIPO .

*Primary Examiner*—Bernard Dentz
*Attorney, Agent, or Firm*—Jacobson, Price, Holman & Stern, PLLC

[57] ABSTRACT

The invention relates to certain substituted imidazo[1,2-a] pyridines useful in the treatment of gastro-intestinal disorders.

12 Claims, No Drawings

3-METHYLIMIDAZOPYRIDINES

This is a 371 of PCT/EP97/00333 filed Jan. 24, 1997.

FIELD OF APPLICATION OF THE INVENTION

The invention relates to novel 3-methylimidazopyridines which are to be used in the pharmaceutical industry as active compounds for the production of medicaments.

KNOWN TECHNICAL BACKGROUND

In European Patent Application EP-A-0 033 094, imidazo-[1,2-a]pyridines are described which carry an aryl substituent in the 8-position, which is preferably a phenyl radical, thienyl radical, pyridyl radical or a phenyl radical substituted by chlorine, fluorine, methyl, tert-butyl, trifluoromethyl, methoxy or cyano. Particularly interesting aryl radicals mentioned in EP-A-0 033 094 are the radicals phenyl, o- or p-fluorophenyl, p-chlorophenyl and 2,4,6-trimethylphenyl, of which the radicals phenyl, o- or p-fluorophenyl and 2,4,6-trimethylphenyl are particularly preferred.—In European Patent Applications EP-A-0 204 285, EP-A-0 228 006, EP-A-0 268 989 and EP-A-0 308 917, imidazo[1,2-a]pyridines are described which carry an unsaturated aliphatic radical, in particular a (substituted) alkynyl radical, in the 3-position.—In European Patent Application EP-A-0 266 890, imidazo[1,2-a]pyridines are described which are substituted in the 8-position by an alkenyl, alkyl or cycloalkylalkyl radical.

DESCRIPTION OF THE INVENTION

It has now been found that the compounds described in greater detail below, which differ from the compounds of the prior art, in particular, by the substitution in the 3- or in the 8-position, have surprising and particularly advantageous properties.

The invention relates to compounds of the formula I (see attached formula sheet), in which R0 is 1–4C-alkyl, hydroxymethyl or trifluoromethyl, R1 is 1–4C-alkyl, R2 is hydrogen, 1–4C-alkyl, 1–4C-alkoxy, halogen or trifluoromethyl, R3 is $SO_2$—R6, CO—R7, COO—R8 or CON(R9)R10, R4 is hydrogen, 1–4C-alkyl, 1–4C-alkoxy, halogen or trifluoromethyl, R5 is hydrogen, 1–4C-alkyl, 1–4C-alkoxy or halogen, A is O (oxygen) or NH, R6 is 1–4C-alkyl, aryl, aryl substituted by R16, R17 and R18, aryl-1–4C-alkyl, aryl-1–4C-alkyl substituted in the aryl moiety by R16, R17 and R18, 1–4C-alkyl completely or partly substituted by fluorine, 1–4C-alkyl substituted by —S(O)$_n$—R19 or the radical —$C_qH_{2q-2}$-aryl, or a cyclic substituent selected from the group consisting of thiolane, thiolane oxide or thiolane dioxide, which is unsubstituted or substituted by hydroxyl, R7 is aryl, aryl-1–4C-alkyl, aryl substituted by R16, R17 and R18, or aryl-1–4C-alkyl substituted in the aryl radical by R16, R17 and R18, R8 is 2–4C-alkyl substituted by R11, 1–4C-alkyl substituted by R12, —N=C(R13)R14, 2–4C-alkyl substituted by R15, aryl, the radical —$C_qH_{2q-1}$ or aryl substituted by R16, R17 and R18, R9 is hydrogen or 1–4C-alkyl, R10 is 2–4C-alkyl substituted by R11, 1–4C-alkyl substituted by R12, or 1–4C-alkyl, R11 is 1–4C-alkoxy, 1–4C-alkylcarbonyloxy, hydroxyl, hydroxy-2–4C-alkoxy or 1–4C-alkoxy-1–4C-alkoxy, R12 is 1–4C-alkoxycarbonyl, 1–4C-alkylcarbonyl, carboxyl, mono-1–4C-alkylaminocarbonyl, di-1–4C-alkylaminocarbonyl, thienyl, pyridyl, aryl or aryl substituted by R16, R17 and R18, R13 is 1–4C-alkyl, phenyl or phenyl-1–4C-alkyl and R14 is 1–4C-alkyl, phenyl or phenyl-1–4C-alkyl, or in which R13 and R14 together are a 4–6C-alkylene group, R15 is phthalimidyl or —S(O)$_n$—R19, where Aryl is phenyl or naphthyl and R16 is hydrogen, halogen, nitro, 1–4C-alkyl, 1–4C-alkoxy, trifluoromethyl, hydroxyl, carboxyl, 1–4C-alkoxycarbonyl, cyano, 1–4C-alkoxy completely or partly substituted by fluorine, phenyl, benzoyl, mono- and di-1–4C-alkylamino, amino, 1–4C-alkylcarbonylamino or S(O)$_n$—R19, R17 is hydrogen, halogen, 1–4C-alkoxy, nitro, carboxyl, 1–4C-alkyl or hydroxyl and R18 is hydrogen or halogen, R19 is 1–4C-alkyl, n is the numbers 0, 1 or 2, q is the numbers 2 or 3, and their salts, and the N-oxides of the pyridines and their salts.

Halogen within the meaning of the invention is bromine, chlorine and fluorine.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and, in particular, the methyl radical.

1–4C-Alkoxy represents an oxygen atom to which one of the abovementioned 1–4C-alkyl radicals is bonded. Examples which may be mentioned are the methoxy, the ethoxy, the propoxy and the butoxy radical.

Aryl-1–4C-alkyl represents one of the abovementioned 1–4C-alkyl radicals which is substituted by phenyl or naphthyl.

Examples of 1–4C-alkyl completely or partly substituted by fluorine which may be mentioned are the 1,2,2-trifluoroethyl, the 2,2,3,3,3-pentafluoropropyl, the perfluoroethyl, the 1,1,2,2-tetrafluoroethyl, the trifluoromethyl, the difluoromethyl and the 2,2,2-trifluoroethyl radical.

Phenyl-1–4C-alkyl represents one of the abovementioned 1–4C-alkyl radicals substituted by phenyl. Examples which may be mentioned are the phenethyl and the benzyl radical.

Exemplary phenyl radicals substituted by R16, R17 and R18 which may be mentioned are the radicals 2-bromophenyl, 4-bromophenyl, 4-benzoylphenyl, 2-chlorophenyl, 3-chlorophenyl, 4-chlorophenyl, 3-bromophenyl, 2,3-dichlorophenyl, 2,4-dichlorophenyl, 2-chloro-5-nitrophenyl, 4-chloro-3-nitrophenyl, 2,6-dichlorophenyl, 3-fluorophenyl, 2,4-difluorophenyl, 2-fluoro-5-nitrophenyl, 2,3-dimethoxyphenyl, 2,4-dimethoxyphenyl, 2-methylphenyl, 3-methylphenyl, 4-methylphenyl, 4-methyl-3-nitrophenyl, 2,4-dimethylphenyl, 2-nitrophenyl, 3-nitrophenyl, 4-nitrophenyl, 2,4-dinitrophenyl, 3,4-dinitrophenyl, 3,5-dinitrophenyl, 2,6-dinitrophenyl, 4-methoxyphenyl, 3-methoxyphenyl, 4-ethoxyphenyl, 3-hydroxyphenyl, 3-trifluoromethylphenyl and 4-trifluoromethylphenyl.

2–4C-Alkyl represents an alkyl radical having 2 to 4 carbon atoms. Examples which may be mentioned are the ethyl, the propyl and the butyl radical.

1–4C-Alkoxycarbonyl represents a radical which, in addition to the carbonyl group, contains one of the abovementioned 1–4C-alkoxy radicals. Examples which may be mentioned are the methoxycarbonyl and the ethoxycarbonyl radical.

1–4C-Alkylcarbonyl represents a radical which, in addition to the carbonyl group, contains one of the abovementioned 1–4C-alkyl radicals. An example which may be mentioned is the acetyl radical.

1–4C-Alkylcarbonyloxy represents a radical which, in addition to the carbonyloxy radical, contains one of the abovementioned 1–4C-alkyl radicals. An example which may be mentioned is the acetyloxy radical.

Mono- and di-1–4C-alkylamino contain, in addition to the nitrogen atom, one or two of the abovementioned 1–4C-alkyl radicals. Di-1–4C-alkylamino is preferred and in particular here dimethyl-, diethyl- or diisopropylamino.

Mono- and di-1–4C-alkylaminocarbonyl contain, in addition to the carbonyl group, one of the abovementioned mono- or di-1–4C-alkylamino radicals. Examples which may be mentioned are the N-methyl, the N,N-dimethyl, the N-ethyl, the N-propyl, the N,N-diethyl and the N-isopropylcarbamoyl radical.

Hydroxy-2–4C-alkoxy represents one of the abovementioned 2–4C-alkoxy radicals which is substituted by a hydroxyl group. An example which may be mentioned is the 2-hydroxyethoxy radical (—O—CH$_2$—CH$_2$—OH).

1–4C-Alkoxy-1–4C-alkoxy represents one of the abovementioned 1–4C-alkoxy radicals which is substituted by a further 1–4C-alkoxy radical. Examples which may be mentioned are the radicals 2-(methoxy)ethoxy-(—O—CH$_2$—CH$_2$—O—CH$_3$), and 2-(ethoxy)ethoxy-(—O—CH$_2$—CH$_2$—O—CH$_2$—CH$_3$).

4–6C-Alkylene represents straight-chain or branched alkylene radicals having 4 to 6 carbon atoms. Examples which may be mentioned are the radicals tetramethylene (—CH$_2$—CH$_2$—CH$_2$—CH$_2$—), pentamethylene (—CH$_2$—CH$_2$—CH$_2$—CH$_2$—CH$_2$—) and hexamethylene [—CH$_2$—(CH$_2$)$_4$—CH$_2$—].

Examples of 1–4C-alkoxy completely or partly substituted by fluorine which may be mentioned are the 1,2,2-trifluoroethoxy, the 2,2,3,3,3-pentafluoropropoxy, the perfluoroethoxy, the 1,1,2,2-tetrafluoroethoxy, the trifluoromethoxy, the difluoromethoxy and the 2,2,2-trifluoroethoxy radical.

1–4C-Alkylcarbonylamino represents an amino group which is substituted by one of the abovementioned 1–4C-alkylcarbonyl radicals. An example which may be mentioned is the acetamido radical (H$_3$C—CO—NH—).

The group —C$_q$H$_{2q-1}$ represents, for example, the isopropenyl radical. The group —C$_q$H$_{2q-2}$-aryl preferably represents the 2-phenylvinyl radical.

Exemplary radicals —S(O)$_n$—R19 which may be mentioned are the methylthio, ethylthio, propylthio, butylthio, methylsulfinyl, ethylsulfinyl, propylsulfinyl, butylsulfinyl, methylsulfonyl, ethylsulfonyl, propylsulfonyl and butylsulfonyl radical.

Exemplary 2–4C-alkyl radicals substituted by R11 are 2-(methoxy)ethyl, 2-(ethoxy)ethyl, 2-(propoxy)ethyl, 2-(butoxy)ethyl, 3-(methoxy)propyl, 3-(ethoxy)propyl, 3-(propoxy)propyl, 3-(butoxy)propyl, 2-(acetyloxy)ethyl, 2-(ethylcarbonyloxy)ethyl, 2-(propylcarbonyloxy)ethyl, 3-(acetyloxy)propyl, 3-(ethylcarbonyloxy)propyl, 3-(propylcarbonyloxy)propyl, 2-hydroxyethyl, 3-hydroxypropyl, 2-(2-hydroxyethoxy)ethyl, 2-(3-hydroxypropoxy)ethyl, 3-(2-hydroxyethoxy)propyl, 2-[2-(methoxy)ethoxy)]ethyl, 2-[2-(ethoxy)ethoxy]ethyl and 4-hydroxybutyl.

Exemplary 1–4C-alkyl radicals substituted by R12 are (methoxycarbonyl) methyl, (ethoxycarbonyl) methyl, (propoxycarbonyl)methyl, 2-(methoxycarbonyl)ethyl, 2-(ethoxycarbonyl)ethyl, 2-(propoxycarbonyl)ethyl, 3-(methoxycarbonyl)propyl, 2-oxopropyl, 2-oxobutyl, 2-oxopentyl, 3-oxobutyl, 3-oxopentyl, 3-oxohexyl, 4-oxopentyl, 4-oxohexyl, 4-oxoheptyl, carboxymethyl, 2-carboxyethyl, 3-carboxypropyl, 4-carboxybutyl, (N-methylcarbamoyl)methyl, (N-ethylcarbamoyl)methyl, (N-propylcarbamoyl)methyl, 2-(N-methylcarbamoyl)ethyl, 2-(N-ethylcarbamoyl)ethyl, 2-(N-propylcarbamoyl)ethyl, 3-(N-methylcarbamoyl)propyl, 3-(N-ethylcarbamoyl)propyl, 5 3-(N-propylcarbamoyl)propyl, (N,N-dimethylcarbamoyl)methyl, 2-(N,N-dimethylcarbamoyl)ethyl, 3-(N,N-dimethylcarbamoyl)propyl, (N-ethyl-N-methylcarbamoyl)methyl, 2-(N-ethyl-N-methylcarbamoyl)ethyl, 3-(N-ethyl-N-methylcarbamoyl)propyl, (N,N-diethylcarbamoyl)methyl, 2-(N,N-diethylcarbamoyl)ethyl, 2-thienylmethyl, 2-(2-thienyl)ethyl, 3-thienylmethyl, 2-(3-thienyl)ethyl, 3-(2-thienyl)propyl, 3-(3-thienyl)propyl, (3-hydroxyphenyl)methyl, 2-(3-hydroxyphenyl)ethyl, 3-(3-hydroxyphenyl)propyl, 2-pyridylmethyl, (4-nitrophenyl) methyl, (2-nitro-4,5-dimethoxyphenyl)methyl, 3-pyridylmethyl, 4-pyridylmethyl, 2-(2-pyridyl)ethyl, 3-(2-pyridyl)propyl and 2-(1-pyridyl)ethyl.

Exemplary 2–4C-alkyl radicals substituted by R15 which may be mentioned are 2-(phthalimidyl)ethyl, 3-(phthalimidyl)propyl, 2-(methylthio)ethyl, 2-(ethylthio)ethyl, 2-(propylthio)ethyl, 3-(methylthio)propyl, 3-(ethylthio)propyl, 2-(methylsulfinyl)ethyl, 2-(ethylsulfinyl)ethyl, 2-(propylsulfinyl)ethyl, 2-(methylsulfonyl)ethyl, 2-(ethylsulfonyl)ethyl and 2-(propylsulfonyl)ethyl.

Exemplary radicals —SO$_2$—R$_6$ which may be mentioned are naphthyl-1-, 5-(dimethylamino)naphthyl-1-, naphthyl-2-, phenyl-1-, 2,5-dichlorophenyl-1-, 2-nitrophenyl-1-, 3,5-dichloro-2-hydroxyphenyl-1-, 3-nitrophenyl-1-, 4-bromophenyl-1-, 4-fluorophenyl-1-, 4-chlorophenyl-1-, 4-chloro-3-nitrophenyl-1-, 4-acetamidophenyl-1-, 4-nitrophenyl-1-, 4-methoxyphenyl-1-, 4-carboxyphenyl-1-, 4-methylphenyl-1-, 2-(methoxycarbonyl)phenyl-1-, 3-trifluoromethylphenyl-1-, 2,5-dimethoxyphenyl-1-, 2-methylphenyl-1-, 2,5-dimethylphenyl-1-, 4-(dimethylamino)-3-nitrophenyl-1-, 3-carboxyphenyl-1-, 5-carboxy-2-methoxyphenyl-1-, 5-carboxy-2-chloro-3-nitrophenyl-1-, 3,4-dichlorophenyl-1-, 3-chloro-4-fluorophenyl-1-, 4-ethylphenyl-1-, 4-propylphenyl-1-, 4-isopropylphenyl-1-, 2-fluorophenyl-1-, 3-fluorophenyl-1-, 4-trifluoromethoxyphenyl-1-, 4-trifluoro-methylphenyl-1-, 2,4-difluorophenyl-1-, 5-(diethylamino)naphthyl-1-, 2-chlorophenyl-1-, 2-methyl-5-nitrophenyl-1-, 2-trifluoromethylphenyl-1-, 3-chlorophenyl-1-, 3,5-dichlorophenyl-1-, 3-methylphenyl-1-, 2-chloro-6-methylphenyl-1-, 5-bromo-2-methoxyphenyl-1-, 3,4-dimethoxyphenyl-1-, 2,3-dichlorophenyl-1-, 2-bromophenyl-1-, 3-chloro-2-methylphenyl-1-, 2-chloro-5-trifluoromethylphenyl-1-, 2,6-dichlorophenyl-1-, 3-bromophenyl-1-, 2-trifluoromethoxyphenyl-1-, 4-cyanophenyl-1-, 2-cyanophenyl-1-, 4-butoxyphenyl-1-, 4-acetamido-3-chlorophenyl-1-, 2,4-dichlorophenyl-1-, 2-chloro-4-trifluoromethylphenyl-1-, 2-chloro-4-fluorophenyl-1-, 5-fluoro-2-methylphenyl-1-, 5-chloro-2-methoxyphenyl-1-, 3-carboxy-4-hydroxyphenyl-1-, 2-methoxy-5-methylphenyl-1-, 2,5-dibromophenyl-1-, biphenyl-4-, 2,6-difluorophenyl-1-, 2-methyl-5-(methylsulfonyl)phenyl-1-, 3,5-dicarboxyphenyl-1-, 3-nitro-4-methylphenyl-1-, 2-nitro-4-methoxyphenyl-1-, 3,4-difluorophenyl-1-, 4-butylphenyl-1-, 2-chloro-4-cyanophenyl-1-, 2,3-dimethylphenyl-1-, 4-bromo-2-trifluoromethoxyphenyl-1-, 3-cyanophenyl-1-, 3-chloro-4-methylphenyl-1-, 4-bromo-2-ethylphenyl-1-, 4(methylsulfonyl)phenyl-1-, 2(methylsulfonyl)phenyl-1-, isopropyl-, methyl-, benzyl-, propyl-, ethyl-, 2,2,2-trifluoroethyl-, butyl-, methylsulfonyl-methyl-, (2-nitrophenyl)methyl-, 2-(naphthyl-1-)ethyl-, 2-phenylvinyl-, (thiolane dioxide)-3-yl and (4-hydroxythiolane dioxide)-3-ylsulfonyl.

Exemplary radicals COO—R8 are the propenyl-2-oxycarbonyl, (4-nitrophenyl-1-)oxycarbonyl, (4-nitrophenyl-1-)methoxycarbonyl, (3-hydroxy-phenyl-1-)methoxycarbonyl, (4-methylphenyl)-oxycarbonyl, (4-bromophenyl-1-)oxycarbonyl, (4-fluoro-phenyl-1-)oxycarbonyl, (4-methoxyphenyl-1-)oxycarbonyl, (2-nitrophenyl-1-)oxycarbonyl, (4-methoxycarbonylphenyl-1-)oxycarbonyl, isopropyloxycarbonyl, (4,5-dimethoxy-2-nitrophenyl-1-)-methoxycarbonyl, 2-methoxyethoxycarbonyl, 2-(methylthio)ethoxycarbonyl, 2-(ethylthio)ethoxy-carbonyl, 2-(methylsulfinyl)ethoxycarbonyl, 2-(ethylsulfinyl)ethoxycarbonyl, 2-(methyl-sulfonyl)ethoxycarbonyl, 2-(ethylsulfonyl)ethoxy-carbonyl, 2-(phthalimidyl)ethoxycarbonyl, 2-[2-(methoxy)ethoxy]ethoxycarbonyl, 2-[2-(ethoxy)ethoxy]-ethoxycarbonyl and the 1-methylpropoxycarbonyl radical.

Suitable salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can be obtained initially as process products, for example in the preparation of the compounds according to the invention on an industrial scale, are converted into pharmacologically tolerable salts by processes known to the person skilled in the art.

Preferred compounds of the formula I are those in which
R0 is 1–4C-alkyl, hydroxymethyl or trifluoromethyl,
R1 is 1–4C-alkyl,
R2 is hydrogen, 1–4C-alkyl, 1–4C-alkoxy, halogen or trifluoromethyl,
R3 is $SO_2$—R6, CO—R7, COO—R8 or CON(R9)R10,
R4 is hydrogen, 1–4C-alkyl, 1–4C-alkoxy, halogen or trifluoromethyl,
R5 is hydrogen, 1–4C-alkyl, 1–4C-alkoxy or halogen,
A is O (oxygen) or NH,
R6 is 1–4C-alkyl, aryl, aryl substituted by R16, R17 and R18, aryl-1–4C-alkyl, aryl-1–4C-alkyl substituted in the aryl moiety by P16, R17 and R18, 1–4C-alkyl completely or partly substituted by fluorine, 1–4C-alkyl substituted by —S(O)$_n$—R19 or the radical —$C_qH_{2q-2}$-aryl, or a cyclic substituent selected from the group consisting of thiolane, thiolane oxide or thiolane dioxide, which is unsubstituted or substituted by hydroxyl,
R7 is aryl, aryl-1–4C-alkyl, aryl substituted by R16, R17 and R18, or aryl-1–4C-alkyl substituted in the aryl radical by R16, R17 and R18,
R8 is 2–4C-alkyl substituted by R11, 1–4C-alkyl substituted by R12, —N=C(R13)R14, 2–4C-alkyl substituted by R15, aryl, the radical —$C_qH_{2q-1}$ or aryl substituted by R16, R17 and R18,
R9 is hydrogen or 1–4C-alkyl,
R10 is 2–4C-alkyl substituted by R11, 1–4C-alkyl substituted by R12 or 1–4C-alkyl,
R11 is 1–4C-alkylcarbonyloxy, hydroxyl, hydroxy-2–4C-alkoxy or 1–4C-alkoxyl-4C-alkoxy,
R12 is 1–4C-alkoxycarbonyl, 1–4C-alkylcarbonyl, carboxyl, mono-1–4C-alkylaminocarbonyl, di-1–4C-alkylaminocarbonyl, thienyl, pyridyl, aryl or aryl substituted by R16, R17 and R18,
R13 is 1–4C-alkyl, phenyl or phenyl-1–4C-alkyl and
R14 is 1–4C-alkyl, phenyl or phenyl-1–4C-alkyl, or in which
R13 and R14 together are a 4–6C-alkylene group,
R15 is phthalimidyl or —S(O)$_n$—R19, where
Aryl is phenyl or naphthyl and
R16 is hydrogen, halogen, nitro, 1–4C-alkyl, 1–4C-alkoxy, trifluoromethyl, hydroxyl, carboxyl, 1–4C-alkoxycarbonyl, cyano, 1–4C-alkoxy completely or partly substituted by fluorine, phenyl, benzoyl, mono- and di-1–4C-alkylamino, amino, 1–4C-alkylcarbonylamino or S(O)$_n$—R19,
R17 is hydrogen, halogen, 1–4C-alkoxy, nitro, carboxyl, 1–4C-alkyl or hydroxyl and
R18 is hydrogen or halogen,
R19 is 1–4C-alkyl,
n is the numbers 0, 1 or 2,
q is the numbers 2 or 3,
and their salts, and the N-oxides of the pyridines and their salts.

Further preferred compounds of the formula I are those in which
R0 is 1–4C-alkyl, hydroxymethyl or trifluoromethyl,
R1 is 1–4C-alkyl,
R2 is 1–4C-alkyl or halogen,
R3 is $SO_2$—R6, CO—R7, COO—R8 or CON(R9)R10,
R4 is hydrogen,
R5 is hydrogen,
A is O (oxygen) or NH,
R6 is 1–4C-alkyl, aryl, aryl substituted by R16, aryl-1–4C-alkyl, aryl-1–4C-alkyl substituted in the aryl moiety by R16 or 1–4C-alkyl substituted by S(O)$_n$—R19,
R7 is aryl, aryl-1–4C-alkyl, aryl substituted by R16 or aryl-1–4C-alkyl substituted in the aryl radical by R16,
R8 is 2–4C-alkyl substituted by R11, 1–4C-alkyl substituted by R12, —N=C(R13)R14 or 2–4C-alkyl substituted by R15, aryl or aryl substituted by R16,
R9 is hydrogen,
R10 is 2–4C-alkyl substituted by R11 or 1–4C-alkyl substituted by R12,
R11 is 1–4C-alkoxy, 1–4C-alkylcarbonyloxy, hydroxyl or 1–4C-alkoxy-1–4C-alkoxy,
R12 is 1–4C-alkoxycarbonyl, carboxyl, mono-1–4C-alkylaminocarbonyl, di-1–4C-alkylaminocarbonyl, thienyl, pyridyl, aryl or aryl substituted by R16, R13 is 1–4C-alkyl and
R14 is 1–4C-alkyl,
R15 is phthalimidyl or —S(O)$_n$—R19, where
Aryl is phenyl and
R16 is hydrogen, halogen, nitro, 1–4C-alkyl, 1–4C-alkoxy, hydroxyl, carboxyl, 1–4C-alkoxycarbonyl, benzoyl, mono- and di-1–4C-alkylamino, amino, 1–4C-alkylcarbonylamino or S(O)$_n$—R19,
R19 is 1–4C-alkyl,
n is the numbers 0, 1 or 2,
and their salts.

Particularly preferred compounds of the formula I are those in which
R0 is 1–4C-alkyl,
R1 is 1–4C-alkyl,
R2 is 1–4C-alkyl,
R3 is SO$_2$—R6,CO—R7 or COO—R8,
R4 is hydrogen,
R5 is hydrogen,
A is NH,
R6 is 1–4C-alkyl,
R7 is aryl substituted by R16,
R8 is 2–4C-alkyl substituted by R11, 1–4C-alkyl substituted by R12, —N=C(R13)R14 or 2–4C-alkyl substituted by R15,
R11 is 1–4C-alkoxy or 1–4C-alkoxy-1–4C-alkoxy,
R12 is 1–4C-alkoxycarbonyl, carboxyl, thienyl, pyridyl or aryl substituted by R16,
R13 is 1–4C-alkyl and
R14 is 1–4C-alkyl,
R15 is phthalimidyl or —S(O)$_n$—R19, where
Aryl is phenyl and
R16 is hydroxyl or benzoyl,
R19 is 1–4C-alkyl,
n is the numbers 0, 1 or 2,
and their salts.

Particularly preferred compounds of the formula I to be emphasized are those in which
R0 is 1–4C-alkyl,
R1 is 1–4C-alkyl,
R2 is 1–4C-alkyl,
R3 is COO—R8,
R4 is hydrogen,
R5 is hydrogen,
A is NH,
R8 is 2–4C-alkyl substituted by R11, 1–4C-alkyl substituted by R12, —N=C(R13)R14 or 2–4C-alkyl substituted by R15,
R11 is 1–4C-alkoxy-1–4C-alkoxy,
R12 is 1–4C-alkoxycarbonyl, carboxyl, thienyl, pyridyl or aryl substituted by R16,
R13 is 1–4C-alkyl and
R14 is 1–4C-alkyl,
R15 is —S(O)$_n$—R19, where
Aryl is phenyl and
R16 is hydroxyl,
R19 is 1–4C-alkyl,
n is the numbers 0, 1 or 2,
and their salts.

One embodiment of the particularly preferred compounds of the formula I to be emphasized are those in which
R0 is 1–4C-alkyl,
R1 is 1–4C-alkyl,
R2 is 1–4C-alkyl,
R3 is COO—R8,
R4 is hydrogen,
R5 is hydrogen,
A is NH,
R8 is 2–4C-alkyl substituted by R11 or 2–4C-alkyl substituted by R15,
R11 is 1–4C-alkoxy-1–4C-alkoxy,
R15 is —S(O)$_n$—R19, where
R19 is 1–4C-alkyl,
n is the numbers 0, 1 or 2,
and their salts.

The invention further relates to a process for the preparation of the compounds of the formula I and their salts. The process comprises a) reacting compounds of the formula II (see attached formula sheet), in which R0, R1, R2, R4, R5 and A have the meanings indicated above, with compounds of the formula R3-X, in which R3 has the abovementioned meaning and X is a suitable leaving group, or b) reacting compounds of the formula III (see attached formula sheet), in which R0, R1 and A have the meanings indicated above, with compounds of the formula IV (see attached formula sheet), in which R2, R3, R4 and R5 have the meanings indicated above and X is a suitable leaving group, or c) oxidizing compounds of the formula I, in which R0, R1, R2, R4, R5 and A have the meanings indicated above and the radical R3 contains a sulfide group (—S—), or d) cleaving compounds of the formula I in which R0, R1, R2, R4, R5 and A have the meanings indicated above and the radical R3 contains an ether group (—O—), at the ether group to give the corresponding terminal hydroxide (—OH), and, if desired, then converting the compounds obtained according to a), b), c) or d) into their salts, or, if desired, then liberating the compounds I from salts of the compounds I obtained.

The introduction of the radical R3 into the compounds II according to process variant a) is carried out in a manner familiar per se to the person skilled in the art, for example as described in the following examples. Exemplary compounds of the formula R3-X according to the invention, in which X is a suitable leaving group, are corresponding sulfonyl chlorides, chloroformic acid esters or acid chlorides.

The reaction conditions which are specifically necessary for carrying out the process is familiar to the person skilled in the art on account of his/her expert knowledge.

The reaction of the compounds III with the compounds IV according to process variant b) is likewise carried out in a manner familiar per se to the person skilled in the art, for example analogously using those processes such as are described in the European Patent Applications EP-A-0 268 989 or EP-A-0 308 917.

A suitable leaving group X in compounds of the formula IV is, for example, a halogen atom (preferably chlorine or bromine) or a methanesulfonyloxy group. The reaction is advantageously carried out in the presence of a base (e.g. of an inorganic hydroxide, such as sodium hydroxide, or of an inorganic carbonate, such as sodium carbonate, or of an organic nitrogen base, such as triethylamine, pyridine, collidine or 4-dimethylaminopyridine), it being possible to favor the conduct of the reaction by addition of catalysts, such as alkali metal iodide or tetrabutylammonium bromide.

The oxidation of the sulfides to the sulfoxides or sulfones analogously to process variant c) is carried out under the conditions such as are familiar to the person skilled in the art for the oxidation of sulfides to sulfoxides and sulfones [for this see, for example, J. Drabowicz and M. Mikolajczyk, Organic preparations and procedures int. 14(1–2), 45–89 (1982) or E. Block in S. Patai, The Chemistry of Functional Groups, Supplement E. Part 1, pp. 539–608, John Wiley and Sons (Interscience Publication), 1980]. Possible oxidants are all reagents customarily used for the oxidation of sulfides to sulfoxides and sulfones, in particular peroxyacids, such as, for example, peroxyacetic acid, trifluoroperoxyacetic acid, 3,5-dinitroperoxybenzoic acid, peroxymaleic acid, magnesium monoperoxyphthalate or preferably m-chloroperoxybenzoic acid.

The reaction temperature (depending on the reactivity of the oxidant and degree of dilution) is between −70° C. and the boiling temperature of the solvent used, but preferably between −30° and +20° C. Oxidation with halogens or with hypohalites (e.g. with aqueous sodium hypochlorite solution), which is expediently carried out at temperatures between 0° and 50° C., has also proven advantageous. The reaction is carried out, for example, in inert solvents, e.g. aromatic or chlorinated hydrocarbons, such as benzene, toluene, dichloromethane or chloroform, preferably in esters or ethers, such as ethyl acetate, isopropyl acetate or dioxane, or in alcohols, preferably isopropanol.

The sulfoxides according to the invention are optically active compounds. Depending on the nature of the substituents, there can additionally be further chiral centers in the molecule. The invention therefore includes both the enantiomers and diastereomers and their mixtures and racemates. The enantiomers can be separated (see, for example, WO92/08716) in a manner known per se (for example by preparation and separation of corresponding diastereoisomeric compounds).

Ether cleavage in compounds of the formula I according to variant d) is likewise carried out in a manner known to the person skilled in the art.

Isolation and purification of the substances according to the invention is carried out in a manner known per se, for example, in such a way that the solvent is distilled off in vacuo and the residue obtained is recrystallized from a suitable solvent or subjected to one of the customary purification methods, such as, for example, column chromatography on suitable support material.

Acid addition salts are obtained by dissolving the free base in a suitable solvent, e.g. in water, in a chlorinated hydrocarbon, such as methylene chloride or chloroform, a lower aliphatic alcohol (ethanol, isopropanol), a ketone, such as acetone, or an ether, such as THF or diisopropyl ether, which contains the desired acid, or to which the desired acid is then added.

The salts are obtained by filtering, reprecipitating, precipitating with a nonsolvent for the addition salt or by evaporating the solvent. Salts obtained can be converted by means of alkalization, e.g. using aqueous ammonia solution, into the free bases, which can in turn be converted into acid addition salts. In this manner, pharmacologically intolerable acid addition salts can be converted into pharmacologically tolerable acid addition salts.

The compounds of the formula R3-X, in which X is a suitable leaving group, preferably chlorine, are either known or can be prepared in a known manner. For example, required chloroformic acid esters can be obtained from the corresponding alcohols by reaction with phosgene.

The starting compounds III are disclosed in the European Patent Application EP-A-0299 470 or can be prepared in an analogous manner.

The starting compounds IV can be prepared in an analogous manner as described in the European Patent Application EP-A-0 308 917. Alternatively, the preparation can be carried out starting from compounds of the formula IV, in which R3 has the meaning hydrogen. To this end, these compounds are first converted into the corresponding isocyanate and converted to the desired compound of the formula IV by subsequent reaction with an appropriate amine, oxime or alcohol.

The following examples serve to illustrate the preparation of the compounds according to the invention in greater detail. In particular, the examples also serve to describe the reactions according to process variants a), b), c) and d), and the preparation of selected starting compounds in an exemplary fashion. Likewise, further compounds of the formula I and further starting compounds whose preparation is not explicitly described can be prepared in an analogous manner or in a manner familiar per se to the person skilled in the art using customary process techniques. The abbreviation RT stands for room temperature, h stands for hour(s), min for minute(s), m.p. for melting point, dec. for decomposition and b.p. for boiling point.

The compounds and their salts mentioned in the examples are a preferred subject of the invention.

EXAMPLES

Starting compounds

A1. 2-(N-Phthalimido-2-ethyl) (2-chloromethyl-3-methylphenyl)carbamate

A suspension of 2-chloromethyl-1-isocyanato-3-methylbenzene (1 g) and N-(2-hydroxyethyl)phthalimide (1.07 g) in petroleum ether (b.p. 100–140° C.) (100 ml) is heated to reflux for 8 h and then stirred at RT for a further 16 h. The precipitate is filtered off and washed with a little dichloromethane and diethyl ether. 1.06 g (52%) of the title compound are obtained as a solid of m.p. 176–178° C.

A2. 8-(2-tert-Butoxycarbonylamino-6-methylbenzylamino)-2,3-dimethylimidazo[1,2-a]pyridine 5.5 g of sodium iodide and 8.0 g of sodium carbonate are added at RT to a solution of 8-amino-2,3-dimethylimidazo[1,2-a]pyridine (4.8 g) and 2-tert-butoxycarbonylamino-6-methylbenzyl chloride (9.2 g) in acetone (250 ml) and the mixture is then heated to boiling under reflux for 6 h. After cooling the solution to RT and concentrating it, the residue is dissolved in a mixture of 200 ml of ethyl acetate and 200 ml of water and the organic phase is separated off. After three further extractions with 100 ml each of ethyl acetate, the combined organic phases are dried over magnesium sulfate and then concentrated. The title compound crystallizes as a slightly yellow solid. After chromatographic purification on silica gel (eluent: toluene/dioxane=20:1) and recrystallization from diisopropyl ether, 7.1 g (62%) of the title compound of m.p. 149–152° C. are obtained.

A3. 8-(2-Amino-6-methylbenzylamino)-2,3-dimethylimidazo[1,2-a]pyridine

Method A:

A solution of 8-(6-methyl-2-nitrobenzylamino)-2,3-dimethylimidazo[1,2-a]pyridine (61 g) in methanol (5.5 l) is hydrogenated at RT and under atmospheric pressure for 1.5 h in the presence of 15 g of palladium on active carbon (5%) as a catalyst. After filtering off the catalyst and concentrating, the residue is dissolved in boiling ethyl acetate (2.7 l). After cooling to RT, 51 g (82%) of the title compound of m.p. 206–208° C. are isolated.

Method B:

6.7 g of 8-(2-tert-butoxycarbonylamino-6-methylbenzylamino)-2,3-dimethylimidazo[1,2-a]pyridine are added in portions at 25–30° C. to a mixture of trifluoroacetic acid (30 ml) and anisole (3 ml). After stirring at RT for 30 minutes, the solution is poured into 100 ml of ice water and then treated with 75 ml of 6 N sodium hydroxide solution. The precipitate is filtered off and purified by chromatography on silica gel (solvent: toluene/dioxane=

8:1). After recrystallizing from ethyl acetate, 3.1 g (62%) of the title compound of m.p. 206–208° C. are obtained.

B1. Methoxycarbonylmethyl (2-hydroxymethyl-3-methylphenyl)carbamate

Starting from methoxycarbonylmethyl chloroformate (11.7 g), 2-amino-6-methylbenzyl alcohol (10.5 g) and pyridine (6.2 ml) in dichloromethane (230 ml), 6.8 g (20%) of the title compound, m.p. 70–74° C., are obtained according to the procedure indicated in Example C1, after chromatography on silica gel (eluent: ethyl acetate/petroleum ether 50/70=1:1) and crystallization from diisopropyl ether.

B2. Methoxycarbonylmethyl (2-chloromethyl-3-methylphenyl)carbamate

Methoxycarbonylmethyl (2-hydroxymethyl-3-methylphenyl)carbamate (6.8 g) is introduced in dichloromethane (60 ml) and treated dropwise with thionyl chloride (3.4 ml). The mixture is then stirred at RT for a further 1 h. The solvent is then distilled off and the residue is treated 2 times with dichloromethane (50 ml each) and the mixture is in each case concentrated again on a rotary evaporator. 7 g (96%) of the title compound of m.p. 114–116° C. are obtained.

C1. 2-Chloromethyl-1-isocyanato-3-methylbenzene

2-Amino-6-methylbenzyl alcohol (10.0 g) is dissolved in abs. toluene (200 ml) at 50° C. At this temperature, 45 ml of about 3.5 M ethereal hydrochloric acid are added dropwise during 0.5 h. The resulting suspension is stirred at RT for 2 h. 5.3 ml of thionyl chloride are then added dropwise at this temperature (evolution of gas). The suspension is stirred for a further 16 h and then concentrated on a rotary evaporator (bath temperature 40° C.). The residue is taken up 3 times in 200 ml of toluene in each case and the mixture is repeatedly concentrated. The crystalline residue is suspended in 400 ml of anhydrous toluene and warmed to 50° C. in an oil bath. Trichloromethyl chloroformate (11.3 ml) is then added dropwise. After addition is complete, the mixture is heated to reflux for 5 h until evolution of gas is complete. The toluene is then stripped off in vacuo and the residue is distilled in a high vacuum. 6.55 g (49%) of the title compound are obtained as a colorless liquid of b.p. (0.25 mbar) 92–93° C.

C2. O-(2-Chloromethyl-3-methylphenylaminocarbonyl) acetone oxime

A solution of 2-chloromethyl-1-isocyanato-3-methylbenzene (2 g) and acetone oxime (0.85 g) in n-hexane (20 ml) is stirred at RT for 16 h, a precipitate being deposited during the course of this. After filtration and washing with n-hexane and diethyl ether, 2.4 g (86%) of the title compound are obtained as a solid of m.p. 76–78° C.

C3. 2-(2-Methoxyethoxy)ethyl (2-chloromethyl-3-methylphenyl)carbamate

A solution of 2-chloromethyl-1-isocyanato-3-methylbenzene (2 g) and diethylene glycol monomethyl ether (1.32 g) in n-hexane (50 ml) is heated to reflux for 5 h. After cooling to RT a suspension is obtained. By filtration and washing with n-hexane and diethyl ether, 1.3 g (39%) of the title compound are isolated as a solid of m.p. 78–83° C.

C4. 2-Thienylmethyl (2-chloromethyl-3-methylphenyl) carbamate

2-Chloromethyl-1-isocyanato-3-methylbenzene (2.5 g) and thiophenemethanol (1.57 g) are combined and stirred at RT. When crystallization commences, petroleum ether 50/70 (20 ml) is added and the suspension is stirred for 16 h at RT. After filtration and washing with diethyl ether, 2.57 g (63%) of the title compound are obtained as a solid of m.p. 111–114° C.

C5. 2-Pyridinylmethyl (2-chloromethyl-3-methylphenyl) carbamate

A solution of 2-chloromethyl-1-isocyanato-3-methylbenzene (2.5 g) and 2-hydroxymethylpyridine (1.5 g) in dichloromethane (25 ml) is stirred at RT for 16 h. By concentration on a rotary evaporator (bath temperature 22° C.) and subsequent chromatography on silica gel (eluent: dichloromethane/methanol 13:1), a solution of the title compound is obtained which is concentrated (not crystallization, but decomposition) on a rotary evaporator. (bath temperature 22° C.). The crude product of the title compound obtained is immediately reacted further.

C6. 3-Hydroxybenzyl (2-chloromethyl-3-methylphenyl) carbamate

A mixture of 2-chloromethyl-1-isocyanato-3-methylbenzene (2 g) and 3-hydroxybenzyl alcohol (1.6 g) is warmed to 75° C. in an oil bath for 1 h and then purified by chromatography on silica gel (eluent: dichloromethane/methanol 19:1). 1 g (30%) of the title compound is obtained as a crude product in the form of an amorphous solid.

C7. 2-N-Phthalimidoethyl (2-chloromethyl-3-methylphenyl)carbamate

A suspension of 2-chloromethyl-1-isocyanato-3-methylbenzene (1.0 g) and 2-hydroxyethyl-N-phthalimide (1.07 g) in petroleum ether 100/140 (100 ml) is heated to reflux for 8 h. It is then stirred at RT for a further 16 h. The precipitate is filtered off, washed with a little dichloromethane and with diethyl ether and dried in a high vacuum. 1.06 g (52%) of the title compound are isolated as a pale beige solid. M.p. 176–178° C.

Final products

1. Ethanesulfonic acid [2-(2,3-dimethylimidazo-[1,2-a] pyridin-8-yl-aminomethyl)-3-methylphenyl]-amide A solution of 8-(2-amino-6-methylbenzylamino)-2,3-dimethylimidazo[1,2-a]pyridine (1.86 g), pyridine (1.1 ml) and ethanesulfonyl chloride (1.18 ml) in dichloromethane (40 ml) is stirred at RT for 48 h. The reaction mixture is then diluted with dichloromethane (60 ml), added to water (100 ml) and extracted. The organic phase is washed with sodium hydrogencarbonate solution (60 ml) and with water (60 ml), dried over sodium sulfate and concentrated. By crystallization of the residue from acetone and subsequent filtration, 0.8 g (32%) of the title compound of m.p. 240–242° C. is obtained.

2. n-Propanesulfonic acid [2-(2,3-dimethylimidazo-[1,2-a] pyridin-8-yl-aminomethyl)-3-methylphenyl]-amide A solution of 8-(2-amino-6-methylbenzylamino)-2,3-dimethylimidazo[1,2-a]pyridine (2.5 g), pyridine (1.4 ml) and n-propanesulfonyl chloride (2 ml) in dichloromethane (50 ml) is stirred at RT for 5 days. The reaction mixture is then diluted with dichloromethane (50 ml), added to water and extracted. The organic phase is washed with sodium hydrogencarbonate solution (50 ml) and with water (50 ml), dried over sodium sulfate and concentrated. By crystallization of the residue from acetone and subsequent filtration, 1.8 g (52%) of the title compound of m.p. 245–248° C. are obtained.

3. 8-{2-[(2-Methoxyethoxy-2-ethoxy)carbonylamino]-6-methylbenzylamino}-2-(2,3-dimethylimidazo-[1,2-a] pyridine hydrochloride A suspension of 8-amino-2,3-dimethylimidazo[1,2-a]-pyridine (0.48 g), 2-(2-methoxyethoxy)ethyl (2-chloromethyl-3-methylphenyl)carbamate (0.9 g), sodium carbonate (0.8 g) and sodium iodide (0.15 g) in acetone (20 ml) is stirred at RT for 16 h. The precipitate is then filtered off and washed with acetone, and the filtrate is concentrated on a rotary evaporator. The residue is taken up in sodium hydrogencarbonate solution (50 ml) and extracted with dichloromethane (3×50 ml). The combined organic extracts are washed with water (100 ml), dried over sodium sulfate and concentrated. The residue is purified by chromatographing twice on silica gel (eluent A: dichloromethane/methanol 13:1), eluent B: ethyl acetate) . The main fraction is treated with ethereal hydrochloric acid and concentrated. 0.7 g (50%) of the title compound is obtained as an amorphous solid which sinters at 70–80° C.

4. 8-{2-[O-(Carbamoyl)acetone oxime]-6-methylbenzylamino}-2,3-dimethylimidazo[1,2-a]pyridine A suspension of 8-amino-2,3-dimethylimidazo[1,2-a]pyridine (0.63 g), O-(2-chloromethyl-3-methylphenylcarbonyl)acetone oxime (1 g), sodium carbonate (1.04 g), and sodium iodide (0.2 g) in acetone (20 ml) is stirred at RT for 16 h. The precipitate is filtered off and washed with acetone, and the filtrate is concentrated on a rotary evaporator. The residue is taken up in sodium hydrogencarbonate solution (50 ml) and extracted with dichloromethane (3×50 ml). The combined organic extracts are washed with water (50 ml), dried over sodium sulfate and concentrated. The residue is purified by chromatography on silica gel (eluent: dichloromethane/methanol 13:1). After concentration of the main fraction and crystallization from diethyl ether, 0.92 g (62%) of the title compound of m.p. 138° C. is obtained.

5. 8{2-[(2-Pyridinylmethoxy)carbonylamino]-6-methylbenzylamino}-2,3-dimethylimidazo[1,2-a]pyridine A suspension of 8-amino-2,3-dimethylimidazo[1,2-a]-pyridine (0.58 g), 2-pyridinylmethyl (2-chloromethyl-3-methylphenyl)carbamate (1.04 g), sodium carbonate (0.95 g) and sodium iodide (0.2 g) in acetone (25 ml) is stirred at RT for 16 h. The precipitate is filtered off and washed with acetone, and the filtrate is concentrated on a rotary evaporator. The residue is taken up in sodium hydrogencarbonate solution (40 ml) and extracted with dichloromethane (3×40 ml). The combined organic extracts are washed with water (70 ml), dried over sodium sulfate and concentrated. The residue is purified by chromatography on silica gel (eluent: ethyl acetate). After concentration of the main fraction and crystallization from acetone, 0.4 g (27%) of the title compound of m.p. 163–165° C. is obtained.

6. 8-{2-[(2-Thienylmethoxy)carbonylamino]-6-methylbenzylamino}-2,3-dimethylimidazo[1,2-a]pyridine A suspension of 8-amino-2,3-dimethylimidazo[1,2-a] pyridine (0.68 g), 2-(2-thienylmethyl) (2-chloromethyl-3-methylphenyl)carbamate (1.25 g), sodium carbonate (1.12 g) and sodium iodide (0.16 g) in acetone (40 ml) is stirred at RT for 16 h. The precipitate is filtered off and washed with acetone, and the filtrate is concentrated on a rotary evaporator. The residue is taken up in sodium hydrogencarbonate solution and extracted with dichloromethane (3×50 ml). The combined organic extracts are washed with water (50 ml), dried over sodium sulfate and concentrated. The residue is purified by chromatography on silica gel (eluent: ethyl acetate). After concentration of the main fraction and crystallization from ethyl acetate/diisopropyl ether, 0.61 g (34%) of the title compound of m.p. 146–147° C. is obtained.

7. 8-{2-[(3-Hydroxybenzyloxy)carbonylamino]-6-methylbenzylamino}-2,3-dimethylimidazo[1,2-a]pyridine A suspension of 8-amino-2,3-dimethylimidazo[1,2-a] pyridine (0.63 g), 3-hydroxybenzyl (2-chloromethyl-3-methylphenyl)carbamate (1.2 g), sodium carbonate (1 g) and sodium iodide (0.14 g) in acetone (20 ml) is stirred at RT for 16 h. The precipitate is filtered off, washed with acetone and concentrated. The residue is taken up in sodium hydrogencarbonate solution (40 ml) and extracted with dichloromethane (3×40 ml). The combined organic extracts are washed with water, dried over sodium sulfate and concentrated. The residue is purified by flash chromatography on silica gel (eluent: dichloromethane/methanol 13:1). After concentration of the main fraction and crystallization from acetone, 0.4 g (22%) of the title compound of m.p. 190–193° C. is obtained.

8. 8-{2-[(Hydroxycarbonylmethyloxy)carbonylamino]-6-methylbenzylamino}-2,3-dimethylimidazo[1,2-a]-pyridine hydrochloride A) 8-{2-[(Methoxycarbonylmethoxycarbonylamino]-6-methylbenzylamino}-2,3-dimethylimidazo[1,2-a]pyridine A suspension of 8-amino-2,3-dimethylimidazo[1,2-a] pyridine (2.05 g), methoxycarbonylmethyl (2-chloromethyl-3-methylphenyl)carbamate (3.45 g), sodium carbonate (3.42 g) and sodium iodide (0.59 g) in acetone (60 ml) is stirred at RT for 20 h. The precipitate is filtered off and washed with acetone, and the filtrate is concentrated on a rotary evaporator. The residue is taken up in sodium hydrogencarbonate solution and extracted with dichloromethane (3×70 ml). The combined organic extracts are washed with water (100 ml), dried over sodium sulfate and concentrated. The residue is purified by chromatography on silica gel (eluent: dichloromethane/methanol 13:1). After concentration of the main fraction, 1 g of a foamy product is obtained. This crude product is an about 1:1 substance mixture of 3-[2-(2,3-dimethylimidazo[1,2-a]pyridin-8-ylaminomethyl)-3-methylphenyl]oxazolidin-2,4-diones and the title compound A (eluent for checking quality: dichloromethane/methanol/ammonia=13:1:0.5). This crude product was directly reacted further.

B) 8-{2-[(Hydroxycarbonylmethyloxy)carbonylamino]-6-methylbenzylamino}-2,3-dimethylimidazo[1,2-a]-pyridine hydrochloride The about 50% pure crude product from A) (0.9 g) is dissolved in ethanol (10 ml), treated with a solution of potassium hydroxide (0.15 g) in ethanol (10 ml) and stirred at RT for 21 h. The reaction solution is then concentrated. The residue is taken up in 1 N hydrochloric acid (25 ml) and extracted with dichloromethane (7×20 ml). The combined organic extracts are concentrated and chromatographed on silica gel (eluent: dichloromethane/methanol 13:1 as a gradient to 1:1). The fraction of $R_f$=0.05–0.1 (eluent: dichloromethane/methanol=13:1) is concentrated and dried at 60° C. for 16 h in a high vacuum. 0.2 g (21%) of the title compound of m.p. 114° C. (sinters) is obtained.

9. 2,3-Dimethyl-8-{2-[(2-methylsulfanylethoxy)carbonylamino]-6-methylbenzylamino}imidazo[1,2-a]-pyridine hemifumarate A 20% strength solution of phosgene in toluene (2.8 ml) is diluted with anhydrous dichloromethane (15 ml) and cooled to 0° C. A solution of 2-methylsulfanylethanol (0.46 ml) and N-methylmorpholine (0.59 ml) in anhydrous dichloromethane (10 ml) is then added dropwise. The mixture is kept at 0° C. for a further 15 min, then warmed to RT and stirred for a further 30 min. A suspension of 8-(2-amino-6-methylbenzylamino)-2,3-dimethylimidazo[1,2-a]pyridine (1.0 g) and triethylamine (0.49 ml) in anhydrous dichloromethane (30 ml) is then added dropwise to the solution and it is additionally stirred at RT for 1 h. Aqueous sodium bicarbonate solution (70 ml) is then added and the mixture is stirred for a further 30 min. The organic phase is separated off and the aqueous phase is extracted with dichloromethane (3×50 ml). The combined organic phases are washed with water (50 ml), dried over magnesium sulfate and concentrated. The residue is taken up in a hot solution of fumaric acid (400 mg) in acetone (30 ml) and cooled to 4° C. The precipitate is filtered off and additionally precipitated from a little hot acetone by stirring. After drying in a high vacuum, 0.65 g (47%) of the title compound is isolated as a pale beige crystallizate. M.p. 174–176° C.

10. 2,3-Dimethyl-8-{2-[(2-methylsulfinylethoxy) carbonylamino]-6-methylbenzylamino}imidazo-[1,2-a] pyridine hemifumarate A solution of 2,3-dimethyl-8-{2-[(2-methylsulfanylethoxy)carbonylamino]-6-methylbenzylamino}imidazo-[1,2-a]pyridine (1.0 g) in anhydrous dichloromethane (25 ml) is cooled to 0° C. and treated in portions with m-chloroperoxybenzoic acid (800 mg) and then stirred at 0° C. for a further 15 min. Aqueous sodium bicarbonate solution (25 ml) is then added, the mixture is stirred for a further 10 min, the organic phase is separated off and the aqueous phase is extracted with dichloromethane (3×20 ml). The combined organic phases are washed with water (50 ml), dried over magnesium sulfate and concentrated. To separate off the sulfone, the residue is chromatographed on silica gel (eluent: ethyl acetate/methanol/ammonia=19:1:0.1). The fractions of $R_f$=0.15 are collected and concentrated. The residue is taken up in a hot solution of fumaric acid (150 mg) in acetone (20 ml) and then cooled to 4° C. After filtration and drying in a high vacuum, 0.54 g (46%) of the title compound is isolated as a pale beige crystallizate. M.p. 137–138° C.

11. 2,3-Dimethyl-8-{2-[(2-methylsulfonylethoxy) carbonylamino]-6-methylbenzylamino}imidazo[1,2-a]-pyridine A solution of 2,3-dimethyl-8-{2-[(2-methylsulfanylethoxy)carbonylamino]-6-methylbenzylamino}imidazo-[1,2-a]pyridine (500 mg) in anhydrous dichloromethane (10 ml) is cooled to 0° C. and treated in portions with m chloroperoxybenzoic acid (0.87 g) and then stirred at 0° C. for a further 45 min. Aqueous sodium bicarbonate solution (15 ml) is then added, the mixture is stirred for a further 10 min, the organic phase is separated off and the aqueous phase is extracted with dichloromethane (3×10 ml). The combined organic phases are washed with water (25 ml), dried over magnesium sulfate and concentrated. To separate off by-products, the residue is chromatographed on silica gel (eluent: ethyl acetate/methanol=10:1). The fractions of $R_f$=0.3 are collected and concentrated. The residue is crystallized from ethyl acetate/diisopropyl ether. After filtration and drying in a high vacuum, 250 mg (22%) of the title compound are isolated as a pale beige crystallizate. M.p. 161–162° C.

Commercial utility

The compounds of the formula I and their salts have valuable pharmacological properties which make them commercially utilizable. In particular, they exhibit marked inhibition of gastric acid secretion and an excellent gastric and intestinal protective action in warm-blooded animals. In this connection, the compounds according to the invention are distinguished by a high selectivity of action, a comparatively long duration of action, a good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions (such as, for example, gastric ulcer, duodenal ulcer, gastritis, hyperacidic or medicament-related functional gastropathy), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations. The compounds according to the invention in this case also have an intrinsic action against the bacterium *Helicobacter pylori*.

In their excellent properties, the compounds according to the invention surprisingly prove to be clearly superior to the compounds known from the prior art in various models in which the antiulcerogenic and the antisecretory properties are determined. On account of these properties, the compounds of the formula I and their pharmacologically tolerable salts are outstandingly suitable for use in human and veterinary medicine, where they are used, in particular, for the treatment and/or prophylaxis of disorders of the stomach and/or intestine.

A further subject of the invention are therefore the compounds according to the invention for use in the treatment and/or prophylaxis of the abovementioned diseases. The invention likewise includes the use of the compounds according to the invention for the production of medicaments which are employed for the treatment and/or prophylaxis of the abovementioned diseases.

The invention furthermore includes the use of the compounds according to the invention for the treatment and/or prophylaxis of the abovementioned diseases.

A further subject of the invention are medicaments which contain one or more compounds of the formula I and/or their pharmacologically tolerable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset of action (e.g. a sustained-release form or an enteric form) by means of the appropriate choice of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the compounds and/or salts according to the invention are to be used for the treatment of the abovementioned diseases, the pharmaceutical preparations can also contain one or more pharmacologically active constituents of other pharmaceutical groups, such as antacids, for example aluminum hydroxide, magnesium aluminate; tranquilizers, such as benzodiazepines, for example diazepam; spasmolytics, such as, for example, bietamiverine, camylofin, anticholinergics, such as, for example, oxyphencyclimine, phencarbamide; local anesthetics, such as, for example, tetracaine, procaine; and, if appropriate, also enzymes, vitamins or amino acids.

To be emphasized in this connection is in particular the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, nalidixic acid, penicillins or alternatively bismuth salts) for the control of *Helicobacter pylori*.

Pharmacology

The excellent gastric protective action and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the secretion-inhibiting action on the perfused rat stomach

In Table A which follows, the influence of the compounds according to the invention on the pentagastrin-stimulated acid secretion of the perfused rat stomach after intravenous administration is shown.

TABLE A

| No. | Dose ($\mu$mol/kg i.v.) | Inhibition of acid secretion (%) |
|---|---|---|
| 9 | 3 | 100 |
| 10 | 3 | 100 |
| 11 | 3 | 100 |

Methodology

The abdomen of anesethized rats (CD rat, female, 200–250 g; 1.5 g/kg i.m. urethane) was opened after tracheotomy by a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm physiological NaCl solution was continuously passed through the stomach (0.5 ml/min, pH 6.8–6.9; Braun-Unita 1). The pH (pH meter 632, glass electrode EA 147; φ=5 mm, Metrohm) and, by titration with a freshly prepared 0.01 N NaOH solution to pH 7 (Dosimat 665 Metrohm), the secreted HCl were determined in the effluent in each case collected at an interval of 15 minutes.

The gastric secretion was stimulated by continuous infusion of 1 $\mu$g/kg (=1.65 ml/h) of i.v. pentagastrin (left femoral vein) about 30 min after the end of the operation (i.e. after determination of 2 preliminary fractions). The substances to be tested were administered intravenously in a 1 ml/kg liquid volume 60 min after the start of the continuous pentagastrin infusion.

The body temperature of the animals was kept at a constant 37.8–38° C. by infrared irradiation and heat pads (automatic, stepless control by means of a rectal temperature sensor).

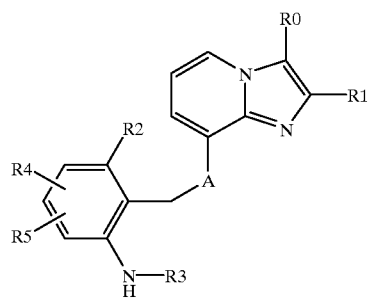

(I)

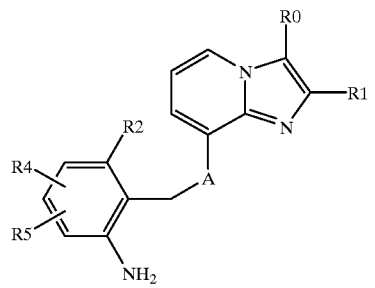

(II)

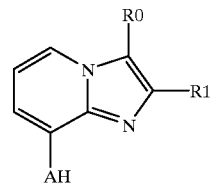

(III)

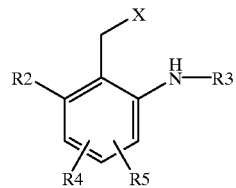

(IV)

What is claimed is:

1. A compound of the formula I

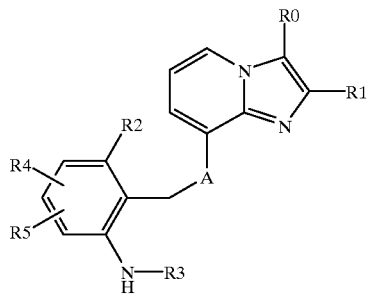

in which

R0 is 1–4C-alkyl, hydroxymethyl or trifluoromethyl,

R1 is 1–4C-alkyl,

R2 is hydrogen, 1–4C-alkyl, 1–4C-alkoxy, halogen or trifluoromethyl,

R3 is $SO_2$—R6,

R4 is hydrogen, 1–4C-alkyl, 1–4C-alkoxy, halogen or trifluoromethyl,

R5 is hydrogen, 1–4C-alkyl, 1–4C-alkoxy or halogen,

A is O (oxygen) or NH,

R6 is 1–4C-alkyl, aryl, aryl substituted by R16, R17 and R18, aryl-1–4C-alkyl, aryl-1–4C-alkyl substituted in the aryl moiety by R16, R17 and R18, 1–4C-alkyl completely or partly substituted by fluorine, 1–4C-alkyl substituted by —S(O)$_n$—R19 or the radical —$C_qH_{2q-2}$-aryl, or a cyclic substituent selected from the group consisting of thiolane, thiolane oxide or thiolane dioxide, which is unsubstituted or substituted by hydroxyl, R7 is aryl, aryl-1–4C-alkyl, aryl substituted by R16, R17 and R18, or aryl-1–4C-alkyl substituted in the aryl radical by R16, R17 and R18, R8 is 2–4C-alkyl substituted by R11, 1–4C-alkyl substituted by R12, —N=C(R13)R14, 2–4C-alkyl substituted by R15, aryl, the radical —$C_qH_{2q-1}$ or aryl substituted by R16, R17 and R18, R9 is hydrogen or 1–4C-alkyl, R10 is 2–4C-alkyl substituted by R11, 1–4C-alkyl substituted by R12, or 1–4C-alkyl, R11 is 1–4C-alkoxy, 1–4C-alkylcarbonyloxy, hydroxyl, hydroxy-2–4C-alkoxy or 1–4C-alkoxy-1–4C-alkoxy, R12 is 1–4C-alkoxycarbonyl, 1–4C-alkylcarbonyl, carboxyl, mono-1–4C-alkylaminocarbonyl, di-1–4C-alkylaminocarbonyl, thienyl, pyridyl, aryl or aryl substituted by R16, R17 and R18, R13 is 1–4C-alkyl, phenyl or phenyl-1–4C-alkyl and R14 is 1–4C-alkyl, phenyl or phenyl-1–4C-alkyl, or in which R13 and R14 together are a 4–6C-alkylene group, R15 is phthalimidyl or —S(O)$_n$—R19, where Aryl is phenyl or naphthyl and R16 is hydrogen, halogen, nitro, 1–4C-alkyl, 1–4C-alkoxy, trifluoromethyl, hydroxyl, carboxyl, 1–4C-alkoxycarbonyl, cyano, 1–4C-alkoxy completely or partly substituted by fluorine, phenyl, benzoyl, mono- and di-1–4C-alkylamino, amino, 1–4C-alkylcarbonylamino or S(O)$_n$——R19, R17 is hydrogen, halogen, 1–4C-alkoxy, nitro, carboxyl, 1–4C-alkyl or hydroxyl and R18 is hydrogen or halogen, R19 is 1–4C-alkyl, n is the numbers 0, 1 or 2, q is the numbers 2 or 3, and their salts, and the N-oxides of the pyridines or a salt thereof.

2. A medicament composition comprising an effective amount of a compound according to claim 1 or a pharmacologically tolerable salt thereof in combination with a customary pharmaceutical auxiliary or excipient.

3. In the prevention or treatment of a gastrointestinal disease by administering an effective amount of suitable active component to a subject prone to or afflicted with such disease, the improvement wherein the suitable active component is a compound according to claim 1 or a pharmacologically tolerable salt thereof.

4. In a method for compounding a medicament composition having an active component for preventing or treating a gastrointestinal disease, the improvement wherein the active component is a compound according to claim 1 or a pharmacologically tolerable salt thereof.

5. A compound of formula I

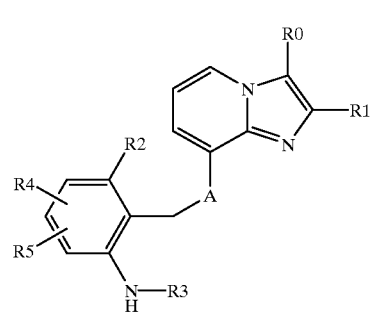

in which

R0 is 1–4C-alkyl,

R1 is 1–4C-alkyl,

R2 is 1–4C-alkyl,

R3 is COO—R8,

R4 is hydrogen,

R5 is hydrogen,

A is NH;

R8 is 2–4C-alkyl substituted by R11, 1–4C-alkyl substituted by R12, —N=—C(R13)R14 or 2–4C-alkyl substituted by R15, R11 is 1–4C-alkoxy-1–4C-alkoxy, R12 is 1–4C-alkoxycarbonyl, carboxyl, thienyl, pyridyl, or aryl substituted by R16, R13 is 1–4C-alkyl, R14 is 1–4C-alkyl, R15 is —S(O)$_n$—R19, where Aryl is phenyl and R16 is hydroxyl, R19 is 1–4C-alkyl, n is a number 0, 1 or 2, or a salt thereof, or an N-oxide of a pyridine or a salt thereof.

6. A compound of formula I according to claim 1 wherein R6 is 1–4C-alkyl.

7. A medicament composition comprising an effective amount of a compound according to claim 5 or a pharmacologically tolerable salt thereof in combination with a customary pharmaceutical auxiliary or excipient.

8. In the prevention or treatment of a gastrointestinal disease by administering an effective amount of suitable active component to a subject prone to or afflicted with such disease, the improvement wherein the suitable active component is a compound according to claim 5 or a pharmacologically tolerable salt thereof.

9. In a method for compounding a medicament composition having an effective component for preventing or treating a gastrointestinal disease, the improvement wherein the active component is a compound according to claim 5 or a pharmacologically tolerable salt thereof.

10. A medicament composition comprising an effective amount of a compound according to claim 6 or a pharmacologically tolerable salt thereof in combination with a customary pharmaceutical auxiliary or excipient.

11. In the prevention or treatment of a gastrointestinal disease by administering an effective amount of suitable active component to a subject prone to or afflicted with such disease, the improvement wherein the suitable active component is a compound according to claim 6 or a pharmacologically tolerable salt thereof.

12. In a method for compounding a medicament composition having an effective component for preventing or treating a gastrointestinal disease, the improvement wherein the active component is a compound according to claim 6 or a pharmacologically tolerable salt thereof.

* * * * *